United States Patent
Quetel et al.

(10) Patent No.: US 7,867,440 B2
(45) Date of Patent: Jan. 11, 2011

(54) METHOD AND INSTALLATION FOR DECONTAMINATING PREFORM NECKS

(75) Inventors: François Quetel, Octeville-sur-Mer (FR); Patrick Mie, Octeville-sur-Mer (FR)

(73) Assignee: Sidel Participations, Octeville-sur-Mer (FR)

( * ) Notice: Subject to any disclaimer, the term of this patent is extended or adjusted under 35 U.S.C. 154(b) by 685 days.

(21) Appl. No.: 10/509,746

(22) PCT Filed: Mar. 28, 2003

(86) PCT No.: PCT/FR03/00986

§ 371 (c)(1), (2), (4) Date: Dec. 23, 2004

(87) PCT Pub. No.: WO03/084818

PCT Pub. Date: Oct. 16, 2003

(65) Prior Publication Data

US 2005/0118057 A1  Jun. 2, 2005

(30) Foreign Application Priority Data

Apr. 4, 2002 (FR) .................................. 02 04202

(51) Int. Cl.
*A61L 2/00* (2006.01)
(52) U.S. Cl. ....................................................... 422/24
(58) Field of Classification Search ................... 422/24, 422/28, 302, 304; 264/532
See application file for complete search history.

(56) References Cited

U.S. PATENT DOCUMENTS

| | | | |
|---|---|---|---|
| 4,375,145 A | 3/1983 | Mosse et al. | |
| 5,129,212 A | 7/1992 | Duffey et al. | |
| 5,186,307 A * | 2/1993 | Doudement et al. | 198/454 |
| 6,145,276 A | 11/2000 | Palm et al. | |
| 6,183,691 B1 * | 2/2001 | Swank et al. | 422/24 |
| 2002/0159915 A1 * | 10/2002 | Zelina et al. | 422/3 |

FOREIGN PATENT DOCUMENTS

| | | | |
|---|---|---|---|
| EP | 0 342 690 A | | 11/1989 |
| JP | 06-171697 | * | 6/1994 |
| WO | WO 95/11765 A | | 5/1995 |
| WO | WO99/03667 | * | 1/1999 |

* cited by examiner

*Primary Examiner*—Walter D Griffin
*Assistant Examiner*—Shanta G Doe
(74) *Attorney, Agent, or Firm*—Sughrue Mion, PLLC

(57) ABSTRACT

The invention concerns decontamination of the neck of thermoplastic performs (4) designed for making containers through a blow forming or extrusion blow molding process, when feeding (in A) the performs (4) sequentially into a unit (B) for manufacturing containers, which consists in passing the neck of the performs (4) through a mist (in 9) of a decontaminating product, then in subjecting the neck of the performs (4) wetted by the decontaminating products to the action of an ultraviolet radiation (in 7) for a least a predetermined minimum time interval.

5 Claims, 3 Drawing Sheets

US 7,867,440 B2
1

METHOD AND INSTALLATION FOR DECONTAMINATING PREFORM NECKS

FIELD OF THE INVENTION

The present invention deals generally with the field of the decontamination (or lowering of the level of contamination) of thermoplastic (especially PET) preforms intended for making into containers such as bottles and the like, by a blow molding or stretch-blow molding process, and it relates more specifically to improvements to the step of decontaminating the necks of these preforms.

DESCRIPTION OF THE PRIOR ART

For the manufacture of decontaminated containers out of thermoplastics, it is known practice to decontaminate the preforms at the beginning of the container manufacturing process, rather than to decontaminate the finished containers, at the end of their manufacturing process, in order to greatly reduce the amount of decontaminating product used (this amount being a function of the surface area to be treated).

As an example, document FR-A-2 766 121 discloses a method and an installation for decontaminating preforms which involve wetting the bodies of the preforms by dipping them into a bath of a decontaminating product such as hydrogen peroxide, and then thermally activating this decontaminating product by heating the preform (the activation of the decontaminating product may take place, in particular, in the oven in which the preforms are heated to prepare them for blow molding).

However, effective decontamination of preforms requires that the whole of each preform be decontaminated, that is to say not only its body but also its neck, and it is known that preforms are made by molding them with their neck in the final shape and having the final dimensions. It is essential that the necks suffer no subsequent thermal stress which would deform the necks and could make it impossible to seal the filled containers afterwards.

For this reason, the decontamination method with thermal activation disclosed in the above-mentioned document can only be applied to the bodies of preforms, and for the same reason, in order to decontaminate the necks, another, non-thermal process is employed which conventionally is decontamination by ultraviolet radiation, involving placing the neck of each preform under ultraviolet radiation for a predetermined period of time. For this purpose, in an actual application, ultraviolet lamps are distributed on either side of an inclined slideway down which the preforms slide by gravity from a feed hopper to a collecting and loading device in the installation, the duration of exposure of the necks to the ultraviolet radiation being determined by the speed of descent of the preforms along the slideway and the slideway's length.

However, the level of decontamination thus achieved is relatively poor (for example of the order of 1 to 1.5 log, that is a reduction by a factor of 10 to 30), although it may be sufficient for some applications.

For other applications, though, which require a higher level of decontamination (for example at least 3 log, that is a reduction by a factor of 1000), the process of decontamination by ultraviolet radiation is insufficient.

Document EP 0 342 690 relates to an installation for, in particular, the sterilization, while they are moving, of containers in the form of pots, in which installation an atomized sterilizing liquid is sprayed onto the containers. However, in that known installation, the sprayed atomized liquid is not channeled and so disperses within the installation and each container is wetted only by the fraction of jet which it happens to intercept. If the containers were not in the form of pots with a large opening but containers with a narrow neck, such as bottles, it would not be certain that the wetting would be uniform and adequate on both the outside and inside of the necks. In addition, such an installation requires a large amount of sterilizing liquid, which pushes up costs.

Document U.S. Pat. No. 5,129,212 relates to a container sterilizing installation equipped with a chamber used both as a place of injection of a sterilizing product and as a place of application of ultraviolet radiation. This known installation has the major drawback that, as soon as it is sprayed, the sterilizing liquid comes under the action of the ultraviolet radiation, and so the product that reaches the containers is already partly denatured. For effective sterilization, therefore, a larger amount of liquid must be dispensed, which is costly.

SUMMARY OF THE INVENTION

It is therefore an object of the invention to improve the process for decontaminating the necks of preforms in such a way that it is possible to achieve a higher level of decontamination than with ultraviolet radiation treatment only, with the additional requirement that the complexity and, most importantly, the size of the whole container manufacturing installation should not be significantly increased.

For this purpose, in accordance with a first aspect thereof, the invention provides a method for decontaminating the necks of thermoplastic preforms intended for making into containers by a blow molding or stretch-blow molding procedure, characterized in that, as the preforms are fed one after the other into a container manufacturing unit, the preforms pass first through an upstream chamber into which a decontaminating liquid is sprayed continuously so as to maintain in this chamber a fog atmosphere of said decontaminating product with which the necks of the preforms are brought into contact, and then pass in front of ultraviolet lamps arranged so as to completely irradiate the necks of the preforms wetted by the decontaminating product for at least a minimum predetermined period of time, before reaching a device that loads them into the manufacturing unit.

Preferably, in order to make the method as effective as possible, the fog is kept flowing through so as to facilitate its renewal.

In a practical embodiment, the decontaminating product is hydrogen peroxide $H_2O_2$, this product being known for its efficiency and its relatively low cost.

By means of the provisions of the invention, the fact that the necks of preforms pass through a fog of decontaminating product results in a wetting of the necks on the outside, on the rim, and partly inside, and there is no need for the liquid to be sprayed in jet form or for the necks to be immersed in a bath of decontaminating liquid as is provided for treating the bodies. The result is that the necks are wetted just as effectively using a smaller amount of liquid and less complicated hardware.

Moreover, the fog is formed upstream of the rows of ultraviolet lamps, which remain in place along the path followed by the necks of the preforms, so that the structural modifications the installation requires are minimal and more especially are entirely localized to the top end of the preform movement means.

Lastly, under the action of the ultraviolet radiation, the decontaminating liquid deposited on the necks of the preforms is activated and the decontamination process is accomplished without any deleterious effect on the shape of the necks.

By way of an example, using a 1% hydrogen peroxide solution, the period of exposure of the necks to the ultraviolet radiation must typically be at least 8 seconds, which means that the length and speed of the movement of the preforms (the speed itself being a function of the speed of operation of the whole installation) must be determined accordingly.

A second aspect of the invention, for the implementation of the above method, is an installation for the decontamination while they are moving of the necks of preforms delivered one after the other to a loading device, said preforms being made of thermoplastic and being intended for making into containers by blow molding or stretch-blow molding, said decontamination installation being structurally and functionally connected to a preform feeder installation comprising means for moving the preforms one after the other, said decontamination installation comprising ultraviolet lamps arranged so that the ultraviolet radiation completely irradiates the necks of the moving preforms, characterized in that the decontamination installation also includes, upstream of the ultraviolet lamps, a chamber traversed by said preform movement means of the feeder installation and in which means are provided for spraying a decontaminating product in such a way as to maintain a fog of the decontaminating product inside said chamber.

Advantageously, the spray means comprise at least two spray nozzles arranged one on either side of the preform movement means and above these, with their respective axes aimed roughly in the direction of the necks of the moving preforms.

Furthermore, for efficient operation, according to the invention suction means are connected to the chamber in order to create a flow through the latter such as to prevent local accumulations of product in suspension.

Depending on the movement means used inside the chamber, they may require the addition of a preform anti-lift member which still allows the fog of decontaminating product to get at the inside walls of the necks of the preforms: in a preferred embodiment, this member may be a rod mounted above the necks of the preforms and of relatively small transverse dimension relative to the diameter of the necks.

The installation in accordance with the invention is thus distinguished by the presence of the fog chamber at the top end of the preform movement means, while further downstream the equipping of the preform movement means with rows of ultraviolet lamps remains unchanged. The result is a very localized addition to the preform feeder installation which requires no modifications either to the upstream part (hopper and one-at-a-time presentation of the preforms), or to the downstream part (ultraviolet radiation treatment and unloading into the installation).

In a preferred embodiment that corresponds to an arrangement of this type of installation, the preform movement means comprise an inclined slideway down which the preforms slide by gravity one after the other and in that this slideway passes through the chamber.

BRIEF DESCRIPTION OF THE DRAWINGS

A clearer understanding of the invention will be gained from a reading of the following detailed description of a preferred embodiment given purely by way of non-restrictive example. This description refers to the attached drawings, in which.

DETAILED DESCRIPTION OF THE INVENTION

Figure 1:
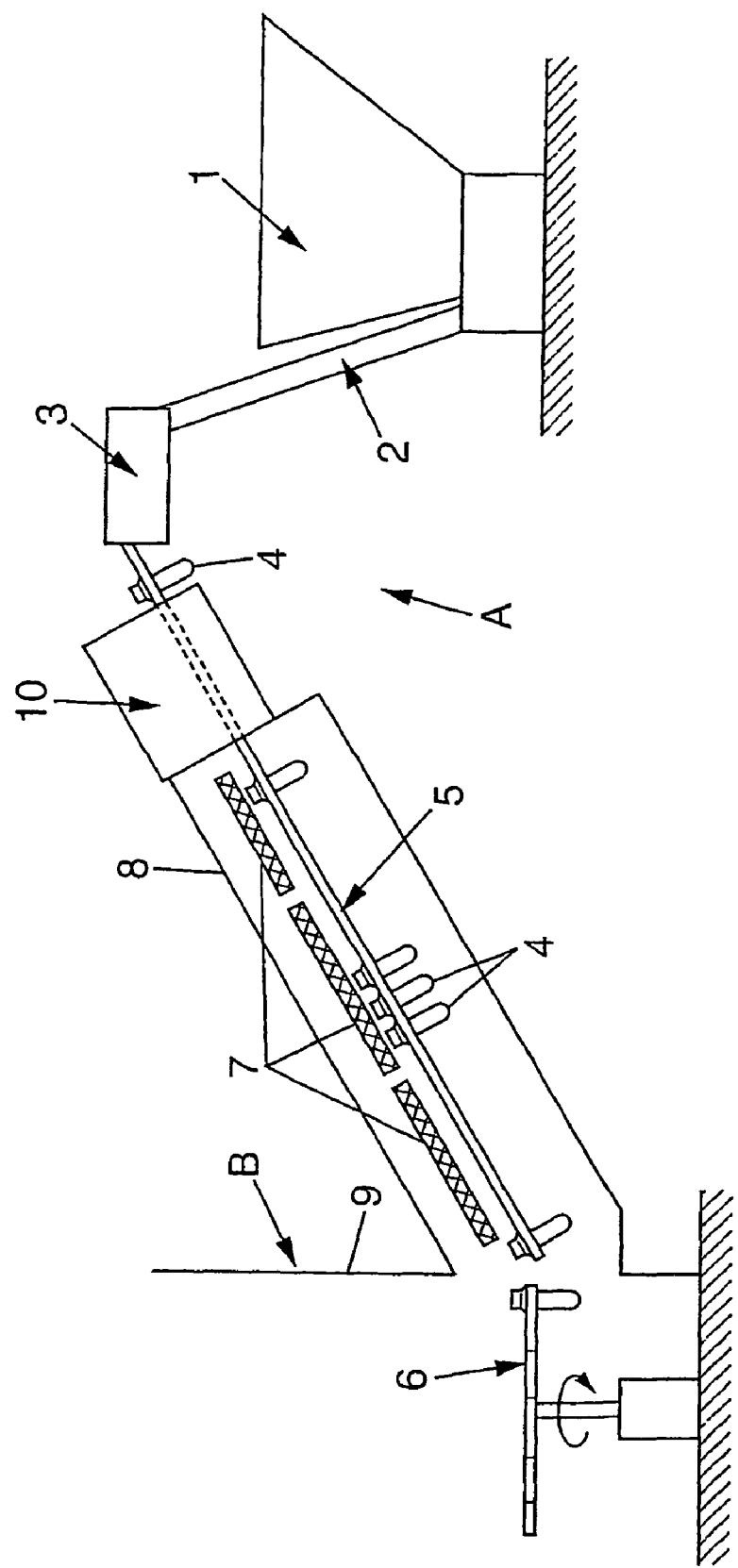
FIG. 1 is a diagrammatic side view of the whole of an installation for decontaminating the necks of preforms, combined with a preform feeder installation, in accordance with the invention.

FIG. 1 shows diagrammatically a preform feeder installation A which represents the input unit to an installation B which makes thermoplastic containers by blow molding or stretch-blow molding.

A conventional arrangement of a feeder installation comprises mainly a hopper 1 into which the preforms, made of a thermoplastic material such as PET, are poured loose, from the base of which hopper the preforms are taken one by one by an elevator device 2 which carries them up to a device 3 which presents them in the correct position, one after the other and vertical, with the neck at the top.

As they come out of the presenting device 3, the preforms 4 move onto an inclined slideway 5 down which they move by gravity, one after the other. The slideway 5 is conventionally constructed from two parallel rails spaced apart from each other. The preforms rest, by an external collar at the base of their neck, in such a way as to straddle the tops of the two rails, while their body is engaged and guided inside the gap between the rails (see the larger-scale view, FIG. 3).

At the bottom end of the slideway 5, the preforms 4, which are presented one at a time, are grasped individually by a gripper device, usually in the form of a loading wheel 6. The loading wheel 6 is in practice the input member to the container manufacturing installation B and typically delivers the preforms to the entrance of a preform heating oven (not shown).

In the case of the installation more particularly envisaged by the invention, which is a decontamination installation, the loading wheel 6 delivers the preforms to a unit (not shown) for decontamination of the preform bodies. This unit may in particular be combined with the preform heating oven as indicated earlier.

For decontamination of the preform necks only—which must not undergo any thermal treatment—rows of ultraviolet lamps 7 are arranged around the slideway 5. These rows of lamps 7 are arranged on either side of the slideway and above the slideway so that the necks of the preforms are completely irradiated (outside, inside and on the rim) by the ultraviolet radiation. To protect the preforms after their treatment, the slideway 5 and the rows of ultraviolet lamps 7 are enclosed in a cowling 8 in the form of a tunnel which connects with the cowling 9 of the installation B, and the whole assembly may advantageously be maintained at an above-atmosphere pressure.

Given the fact that decontaminating the necks of preforms by ultraviolet radiation alone produces only a limited level of decontamination (typically 1 to 1.5 log), a more thorough decontamination (typically 3 log for example) can only be achieved by subjecting the necks of preforms to the action of a decontaminating product such as hydrogen peroxide. To save having to dip the necks of the preforms in a bath of product or spray jets of liquid onto the preform necks—a process which would require complex, large and expensive installations—the invention envisages the use of a fog of decontaminating product through which the necks of the preforms are conveyed: once wetted, the necks pass under the ultraviolet radiation which activates the decontaminating product and produces the required level of decontamination of the necks.

For this purpose, the following means may be added to the installation as described above.

Between the device 3 which correctly presents the preforms to the top entrance of the slideway 5 and the rows of ultraviolet lamps 7, and therefore upstream of said rows of lamps 7, a closed chamber 10 is installed which nonetheless allows for the slideway 5 to pass through it, giving unobstructed passage to the preforms 4. A fog of decontaminating product such as hydrogen peroxide is maintained in the chamber 10 to dampen the outside, the rim and part of the inside of the necks of the preforms 4.

With this arrangement, as the preforms 4 descend the slideway 5, they pass through the fog chamber 10 where their necks are wetted by the decontaminating product, then, downstream of this chamber 10, pass between the rows of ultraviolet lamps 7 where the ultraviolet radiation activates the decontaminating product. The journey of the preform necks beneath the ultraviolet radiation is made long enough to give effective decontamination of the necks of the preforms (e.g. a duration of about 8 seconds with 1% hydrogen peroxide at room temperature).

Figure 2:
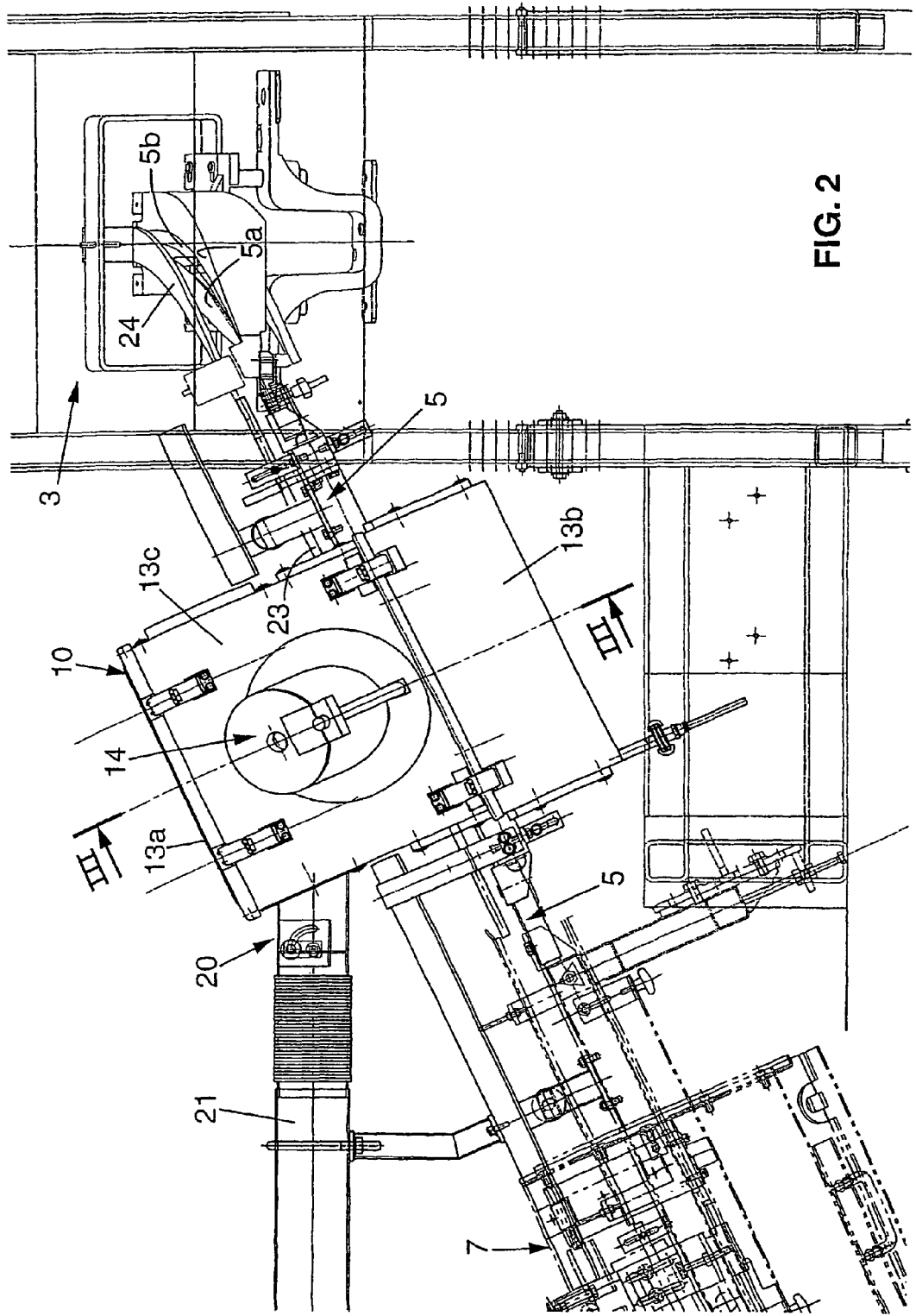
FIG. 2 is a side view of part of the installation of FIG. 1.
Figure 3:
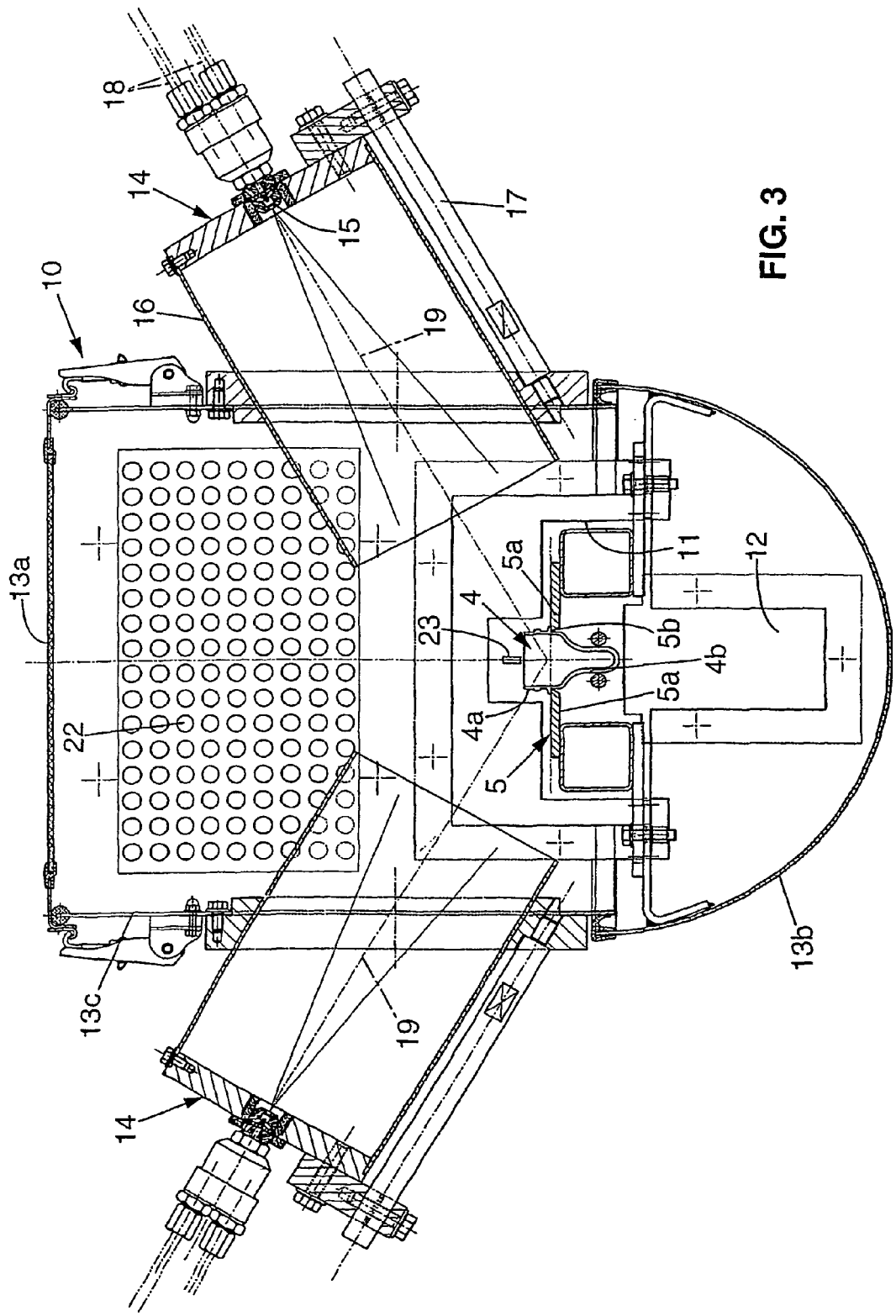
FIG. 3 is a cross section through the fog chamber included in the part of the installation which can be seen in FIG. 2.

The specific arrangement of the chamber 10 is illustrated in detail and on a larger scale in FIG. 2, which is a side view similar to FIG. 1, and to FIG. 3, which is a cross section taken on the line marked III-III in FIG. 2. In these FIGS. 2 and 3, the same reference numbers are used as in FIG. 1 to denote the same members or functional parts. In FIG. 2, the protective cladding 8 has been removed to make the figure more readable. At the top of the slideway 5 which is curved in the embodiment illustrated, notice the two rails 5a on which the preforms 4 visible in FIG. 3 rest via their collars, with their necks 4a on top of the slideway 5 and their bodies 4b engaged in the gap 5b defined between the two rails 5a.

The chamber 10 may be made, for example, of sheet metal and encloses the slideway 5 underneath. Its two end faces are cut open to present two openings 11, one at each end, carefully shaped to allow the preforms to pass through freely. Optionally, removable masks may be provided to close off portions of these openings 11 if the preforms are small (for example the mask 12 provided in the case, illustrated in FIG. 3, of preforms with short bodies).

The chamber 10 may be made by assembling several removable elements (cover 13a, bottom 13b) attached to a main structure 13c, for ease of maintenance.

The chamber 10 is equipped with means 14 for producing a fine spray of the decontaminating product so that a fog of decontaminating product is maintained inside it. There may preferably be a pair of these means 14, one on either side of the slideway 5 as illustrated in FIG. 3. Each of these spray means comprises a fine spray nozzle 15 mounted on the end wall of a cylindrical housing 16 engaged through a main opening in the wall of the main structure 13c of the chamber 10, the housing being fixed to the latter by fixing means 17. The nozzle 15 is connected to a source of pressurized decontaminating product by one or more lines 18.

The two spray means 14 are arranged on either side of and above the slideway 5, essentially symmetrically, with the respective axes 19 of the nozzles 15 essentially coplanar and aimed approximately at the necks 4a of the preforms 4.

These arrangements give a structurally simple setup, the component parts or elements of which are easy to strip and/or easy to get at. Internally, the chamber 10 has few reliefs and few nooks and crannies (in particular, the bottom wall 13b may be half-cylindrical in shape) so that there is less possibility of the product being deposited or the fog being trapped.

To further improve the efficiency of renewal of the fog and rapid and uniform wetting of the necks 4a of the preforms, the chamber 10 may be provided with a suction device 20 (see FIG. 2) consisting, for example, of an opening in the wall of the main structure 13c of the chamber, to which a line 21 connected for example to a suction unit (not visible) is connected. Simultaneously, one of the walls of the chamber may contain a hole (as illustrated at 22 in FIG. 3) to assist flow through the chamber.

It will also be observed that, in order not to impede the movement of the fog of decontaminating product towards the inside walls of the preform necks, there is provided, above the slideway and above the necks 4a of the preforms, an anti-lift member (to prevent preforms being lifted accidentally out of the slideway 5) in the form of a rod 23 of relatively small cross section compared with the diameters of the necks 4a—and not in the form of a relatively wide flat band, as is the case over the rest of the track (see for example the band 24 upstream of the chamber 10 in FIG. 2).

Clearly, the length of the chamber 10 and the number and disposition of the spray means 14 may be adapted to suit the general conditions of operation of the overall container manufacturing installation, particularly as a function of the speed of movement of the preforms along the slideway 5.

The invention claimed is:

1. A method for decontaminating necks of thermoplastic preforms before said performs are blow molded or stretch-blow molded for manufacturing containers, the method comprising:
    providing a pair of rails forming a path, the pair of rails configured to engage said preforms such that said preform necks ride above the pair of rails while bodies of the preforms ride below the rails,
    passing said preforms one after the other through an upstream chamber inside which preform necks move along the path;
    spraying continuously a decontaminating liquid inside said chamber toward said path in such a manner that a fog atmosphere of said decontaminating liquid is maintained inside said chamber with said preform necks being bathed in said fog of decontaminating liquid and with said preform necks having inside and outside surfaces which become wetted by said decontaminating liquid, said fog of decontaminating liquid being caused to flow through said chamber, and
    passing then said preform necks being wetted by said decontaminating liquid in front of ultraviolet lamps arranged downstream of said chamber so that said preform necks become entirely irradiated inside and outside for at least a minimum predetermined period of time,
    wherein the pair of rails are disposed between a spray spraying the decontamination liquid and the bodies of the preforms.

2. The method as claimed in claim 1, wherein the decontaminating product is hydrogen peroxide $H_2O_2$.

3. A decontaminating installation for the decontamination of necks of thermoplastic preforms intended for being blow molded or stretch-blow molded for manufacturing containers, the installation comprising:
    a pair of rails forming an opening configured to engage said preforms such that said preform necks ride above the pair of rails while bodies of the preforms ride below the rails, a preform feeder device which is adapted for moving said preforms one after the other with necks thereof moving along a path, wherein spray means are arranged inside a chamber and directed substantially in the direction of said path for spraying a decontaminating liquid toward said path and in such a way that a fog atmosphere of said decontaminating liquid is maintained inside said chamber, with said preform necks having inside and outside surfaces which become wetted by said decontaminating liquid, wherein suction means are connected to said chamber and are arranged so as to cause said fog of said decontamination liquid to flow through said chamber, wherein an ultraviolet lamp unit is arranged downstream of said chamber so that ultraviolet radiation entirely irradiates said wetted preform necks inside and outside, and wherein said ultraviolet lamp unit has a length and said preform feeder device is adapted for moving said preforms one after the other with a speed that said moving wetted preform necks become entirely irradiated inside and outside for a least a minimum predetermined period of time, wherein the pair of rails is disposed between the spray means and the bodies of the preforms, wherein said preform feeder device inside the chamber includes a rod which has a relatively small transverse dimension relative to the neck diameter and which extends along and above said path so as to be above said preform necks, whereby said rod prevents said preforms being lifted up but allows said fog of decontaminating product to access the inside walls of the preform necks.

4. The installation as claimed in claim 3, wherein the spray means comprise at least two spray nozzles arranged inside said chamber on either side of said path and above said path, said two spray nozzles being respectively directed substantially in the direction of said path.

5. The installation as claimed in claim 3, wherein said preform feeder device comprises an inclined slide guide extending through said chamber and down which said preforms slide by gravity one after the other.

* * * * *